(12) United States Patent
Imamura et al.

(10) Patent No.: US 8,403,852 B2
(45) Date of Patent: Mar. 26, 2013

(54) ULTRASONIC DIAGNOSTIC APPARATUS AND CONTROL METHOD THEREOF

(75) Inventors: Tomohisa Imamura, Nasushiobara (JP); Tetsuya Kawagishi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 280 days.

(21) Appl. No.: 11/252,707

(22) Filed: Oct. 19, 2005

(65) Prior Publication Data

US 2006/0084874 A1     Apr. 20, 2006

(30) Foreign Application Priority Data

Oct. 20, 2004     (JP) ................................ 2004-306019

(51) Int. Cl.
*A61B 8/00* (2006.01)
(52) U.S. Cl. ......................... 600/443; 600/407; 600/437
(58) Field of Classification Search .................. 600/428, 600/437, 443; 73/627, 629, 630
See application file for complete search history.

(56) References Cited

U.S. PATENT DOCUMENTS

| | | | |
|---|---|---|---|
| 4,559,952 A | 12/1985 | Angelsen et al. | |
| 5,873,829 A | 2/1999 | Kamiyama et al. | |
| 6,131,458 A * | 10/2000 | Langdon et al. | ................. 73/627 |
| 6,186,950 B1 * | 2/2001 | Averkiou et al. | ............. 600/443 |
| 6,198,959 B1 * | 3/2001 | Wang | ............................. 600/413 |
| 6,454,714 B1 * | 9/2002 | Ng et al. | ........................ 600/443 |
| 6,905,467 B2 * | 6/2005 | Bradley et al. | ................ 600/443 |
| 2001/0034485 A1 * | 10/2001 | Kawagishi et al. | ........... 600/443 |
| 2003/0060712 A1 * | 3/2003 | Kawagishi et al. | ........... 600/458 |

FOREIGN PATENT DOCUMENTS

JP     2002-296907     10/2002
JP     2003-70935     3/2003

* cited by examiner

*Primary Examiner* — Peter Luong
(74) *Attorney, Agent, or Firm* — Oblon, Spivak, McClelland, Maier & Neustadt, L.L.P.

(57) ABSTRACT

A combined wave having a plurality of frequencies and phases is transmitted to each of a plurality of scan lines in at least three rates by alternately inverting a phase by 180°. An obtained echo signal is received for each rate. The echo signals are added by using arbitrary weighting coefficients so that 0 is obtained by using the polarity as the sign. Ultrasonic image data is generated by using a difference tone component contained in the added echo signal.

13 Claims, 9 Drawing Sheets

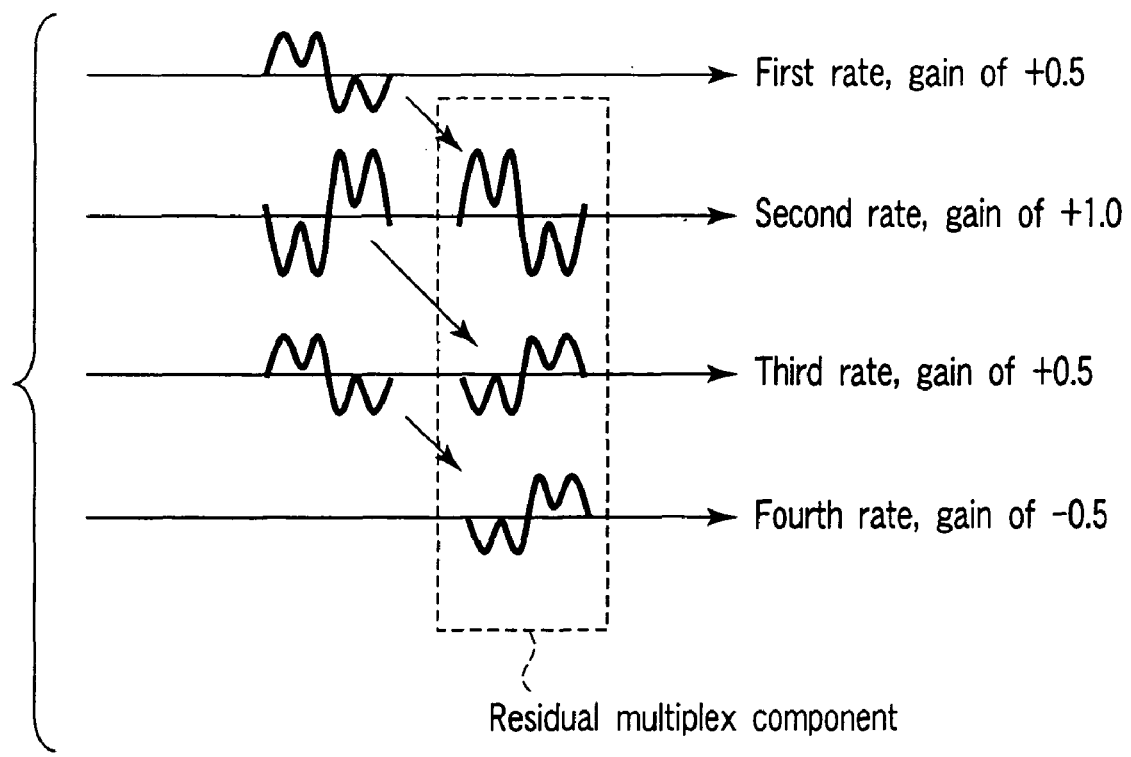
F I G. 7

| Cardiac time phase | First rate | Second rate | Third rate |
|---|---|---|---|
| T$_2$, T$_6$ | 1 | 1 | 0 |
| T$_1$, T$_5$ | 0.3 | 1 | 0.7 |
| T$_4$, T$_8$ | 0.5 | 1 | 0.5 |
| T$_3$, T$_7$ | 0.7 | 1 | 0.3 |
F I G. 9
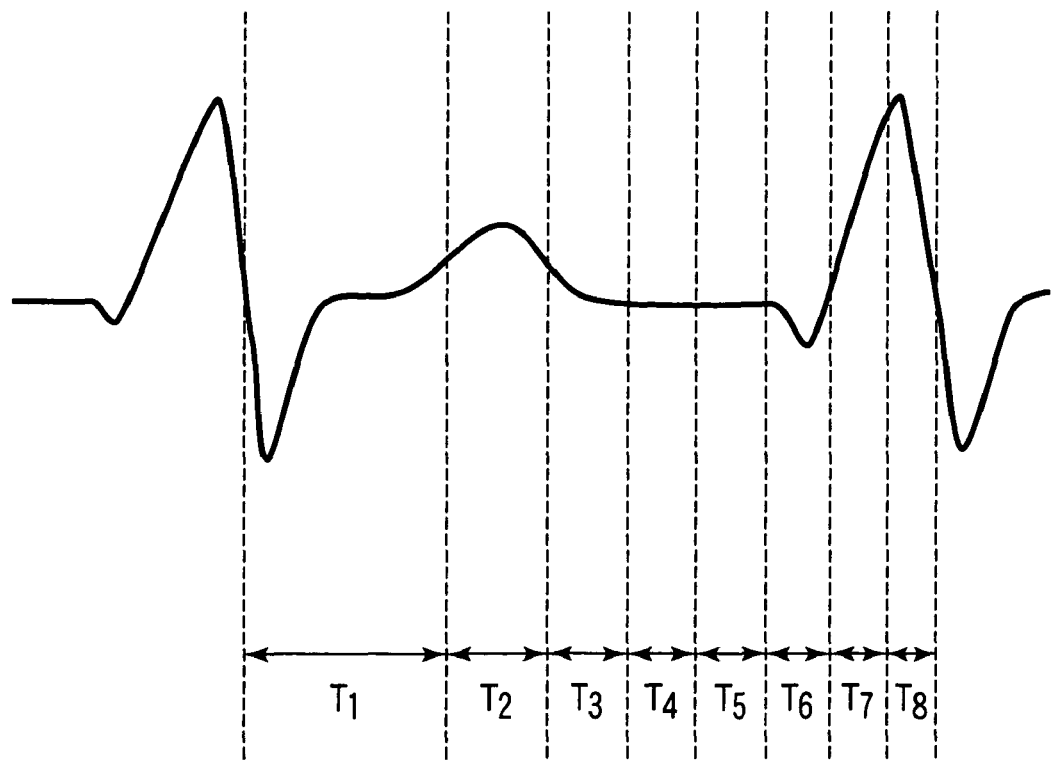
F I G. 10

ULTRASONIC DIAGNOSTIC APPARATUS AND CONTROL METHOD THEREOF

CROSS-REFERENCE TO RELATED APPLICATIONS

This application is based upon and claims the benefit of priority from prior Japanese Patent Application No. 2004-306019, filed Oct. 20, 2004, the entire contents of which are incorporated herein by reference.

BACKGROUND OF THE INVENTION

1. Field of the Invention

The present invention relates to a technique of reducing a motion artifact in executing tissue harmonic imaging (THI) using a difference tone.

2. Description of the Related Art

An ultrasonic diagnostic apparatus is a diagnostic apparatus for displaying an image of in vivo information. The ultrasonic diagnostic apparatus is less expensive and causes no exposure, as compared to other image diagnostic apparatuses such as an X-ray diagnostic apparatus or an X-ray computerized topographic apparatus, and is used as a useful apparatus for noninvasive observation in real time. The ultrasonic diagnostic apparatus has a wide application range because of its characteristics and is used to diagnose circulatory organs such as a heart, abdominal organs such as a liver and kidney, peripheral vessels, cerebral blood vessels or in diagnosis in obstetrics and gynecology.

Recently, various visualization methods using an ultrasonic diagnostic apparatus have been proposed. Typical examples are as follows. In a pulse inversion method, ultrasonic waves are transmitted in two rates with different phases, and obtained echo signals are added to remove the fundamental wave (Iwao Abiru & Tomoo Kamakura, "Nonlinear Propagation of Ultrasonic Pulse", IEICF Technical Report US89-23, p. 53). In another method, one transmission wave is transmitted by controlling a plurality of frequencies and phases, and a harmonic component generated in a frequency band twice the fundamental wave, the difference tone component of the fundamental wave, and the chord component of the fundamental wave are visualized (e.g., Japanese Patent Application No. 2003-070935). In still another method, at least one rate in which the transmission pulse is turned off is inserted after two kinds of ultrasonic pulses obtained by inverting the phase by pulse inversion, and a plurality of reception signals are selectively added for each scan line, thereby reducing superimposition of a residual ultrasonic wave on the echo signal to be used for visualization.

In the above-described THI using a difference tone, the frequency of the difference tone overlaps the fundamental wave frequency. Hence, the difference tone component cannot properly be visualized. In this case, the fundamental wave component can be removed from the difference tone component by using pulse inversion. With this method, excellent diagnostic images can be collected for a part without any motion.

However, when tissue with quick motion (e.g., a heart) is visualized by THI using the difference tone, a motion artifact may be generated by the fundamental wave component. Although the fundamental wave component can be reduced from the difference tone component by using pulse inversion, the motion artifact cannot properly be reduced. When a normal filter is used, the motion artifact does not appear. However, it is impossible to properly remove the fundamental wave component superimposed on the difference tone component.

BRIEF SUMMARY OF THE INVENTION

The present invention has been made in consideration of the above-described situation, and has as its object to provide an ultrasonic diagnostic apparatus and ultrasonic imaging program, which can reduce a fundamental wave component and motion artifact component from a difference tone component in THI using a difference tone.

According to an aspect of the present invention, there is provided an ultrasonic diagnostic apparatus which comprises: a transmission unit which transmits, to each of a plurality of scan lines, transmission ultrasonic wave in at least three rates and including at least a phase inverting by 180°, the transmission ultrasonic wave being formed by combining at least a first fundamental wave and a second fundamental wave as a higher harmonic wave than the first fundamental wave; a reception unit which receives an echo signal based on the transmission ultrasonic wave for each rate; an addition processing unit which adds the echo signals between the rates for each scan line by using predetermined weighting coefficients; and a generation unit which generates ultrasonic image data by using a difference tone component contained in the added echo signal.

According to another aspect of the present invention, there is provided an ultrasonic diagnostic apparatus control method which comprises: transmitting, to each of a plurality of scan lines, transmission ultrasonic wave in at least three rates and including at least a phase inverting by 180°, the transmission ultrasonic wave being formed by combining at least a first fundamental wave and a second fundamental wave as a higher harmonic wave than the first fundamental wave; receiving an echo signal based on the transmission ultrasonic wave for each rate; adding the echo signals between the rates for each scan line by using predetermined weighting coefficients; and generating ultrasonic image data by using a difference tone component contained in the added echo signal.

BRIEF DESCRIPTION OF THE SEVERAL VIEWS OF THE DRAWING

FIG. 7 is a view for explaining ultrasonic transmission/reception which is executed for residual multiplex reduction by the ultrasonic diagnostic apparatus;

FIG. 9 is a table showing an example of a weighting coefficient table which makes cardiac time phases correspond to weighting coefficients in echo signal addition processing;

FIG. 10 is a view showing an ECG waveform so as to explain the concept of adaptive control of the weighting coefficients.

DETAILED DESCRIPTION OF THE INVENTION

Figure 1:
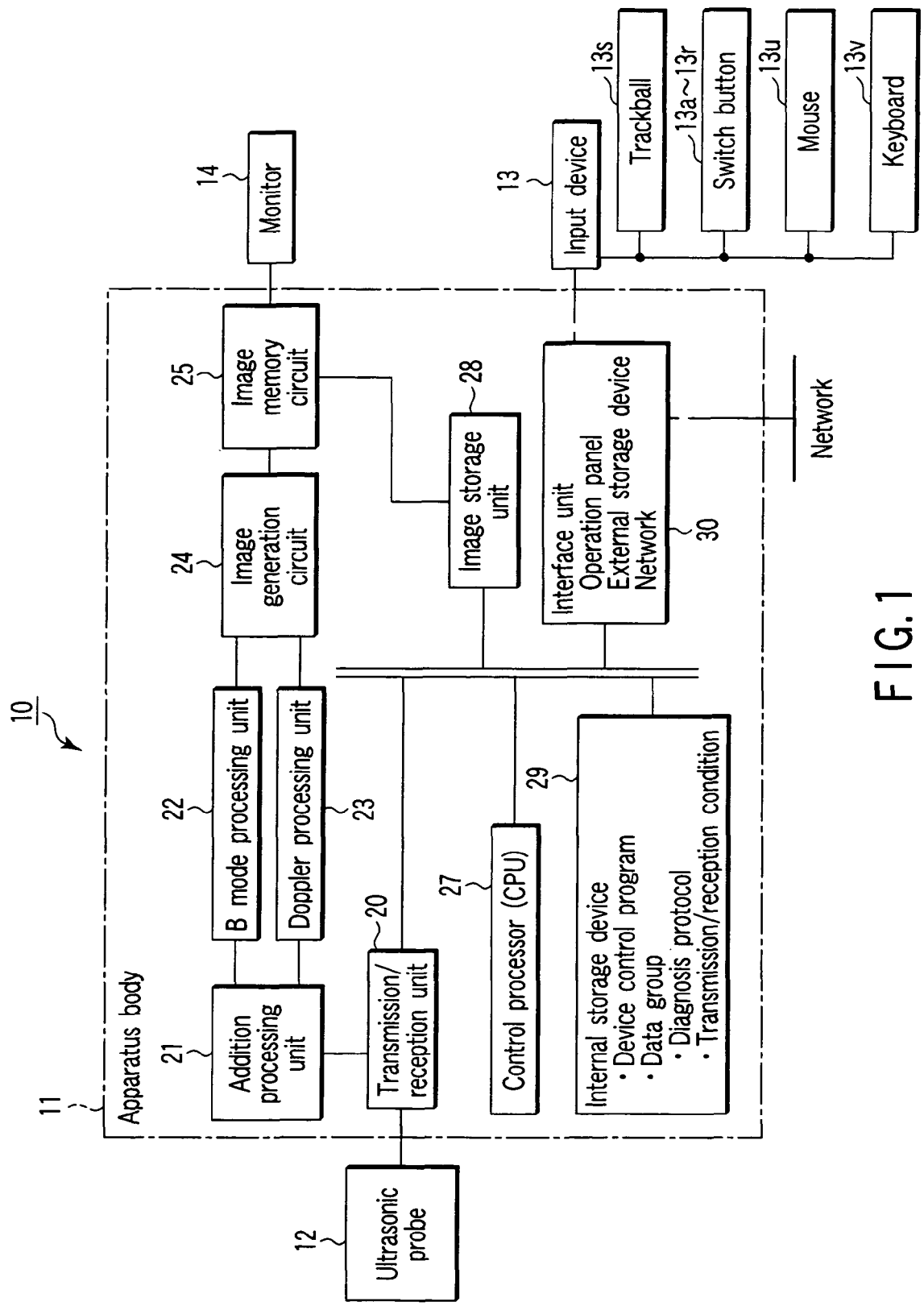
FIG. 1 is a block diagram showing an ultrasonic diagnostic apparatus 10 according to the first embodiment.

The first to third embodiments of the present invention will be described below with reference to the accompanying drawing. In the following description, the same reference numerals denote constituent elements having almost the same function and arrangement, and a repetitive description will be done only when necessary.

First Embodiment

FIG. 1 is a block diagram of an ultrasonic diagnostic apparatus 10 according to this embodiment. As shown in FIG. 1, the ultrasonic diagnostic apparatus 10 includes an ultrasonic probe 12, an apparatus body 11, an external input device 13 which is connected to the apparatus body 11 to input various kinds of instructions, commands, and information from an operator to the apparatus body 11, and a monitor 14. The input device 13 includes a trackball 13s, switch buttons 13a to 13r, mouse 13u, and keyboard 13v to, e.g., set a region of interest (ROI). The apparatus body 11 has an addition processing unit 21, ultrasonic transmission/reception unit 20, B mode processing unit 22, Doppler processing unit 23, image generation circuit 24, image memory circuit 25, control processor (CPU) 27, image storage unit 28, internal storage device 29, and interface unit 30.

The ultrasonic probe 12 has piezoelectric vibrators each serving as an acoustoelectric reversible conversion element of, e.g., piezoelectric ceramics. The plurality of piezoelectric vibrators are juxtaposed and provided at the tip of the probe 12.

The ultrasonic transmission/reception unit 20 reads out transmission/reception conditions which are stored in the internal storage device 29 by the control processor 27 and generates rate pulses in accordance with the transmission/reception conditions. The ultrasonic transmission/reception unit 20 gives, to each rate pulse, a delay time necessary for converging an ultrasonic wave into a beam and determining the transmission directivity and applies a voltage pulse to the probe 12 for each channel. The probe 12 transmits an ultrasonic beam to a subject.

By a selection operation by the user through the input device 13 or another interface, the scan program and device control program stored in the device 29 are read out. In accordance with them, the control processor 27 controls the transmission/reception unit 20.

The ultrasonic beam sent into the subject to generate an image is reflected by the discontinuity surface of acoustic impedance in the subject. The reflected wave is received by the probe 12. An echo signal output from the probe 12 for each channel is received by the transmission/reception unit 20. The echo signal is amplified for each channel, given a delay time necessary for determining the reception directivity, and added in the transmission/reception unit 20. By this addition, a reflection component from a direction corresponding to the reception directivity is enhanced. The total directivity of ultrasonic transmission/reception is determined by the transmission directivity and reception directivity (this directivity is generally called a "scan line").

The addition processing unit 21 adds echo signals received from the transmission/reception unit 20 by using a predetermined weight between rates by gain control for each rate in each scan line. This addition processing will be described later in detail.

The added echo signal output from the addition processing unit 21 is sent to the B mode processing unit 22 and Doppler processing unit 23. The B mode processing unit 22 includes a logarithmic converter, envelop detection circuit, and analog-to-digital (A/D) converter, although they are not illustrated. The logarithmic converter logarithmically converts the echo signal. The envelop detection circuit detects the envelop of the output signal from the logarithmic converter. The detection signal is digitized through the analog-to-digital converter and output as detection data. The Doppler processing unit 23 extracts a blood flow component by using a result of frequency analysis or a filter and obtains blood information such as mean velocities, variances, powers, and the like at multiple points.

The image generation circuit 24 executes frame correlation processing by using the detection data input from the B mode processing unit 22 to generate a B mode image. The image generation circuit 24 also creates a mean velocity image, variance image, power image, and combined image thereof by using the blood flow information input from the Doppler processing unit 23.

The image memory circuit 25 generates an ultrasonic image to be displayed on the monitor 14 on the basis of the image data (also called "raw data") received from the image generation circuit 24. The image memory circuit 25 includes a scan converter, cinememory, frame memory, and video converter. The scan converter converts a scan line signal sequence of ultrasonic scan, which is input from the image generation circuit 24, into data of an orthogonal coordinate system based on spatial information. The cinememory saves, e.g., ultrasonic images corresponding to a plurality of frames immediately before freeze. When images stored in the cinememory are continuously displayed (cinedisplayed), an ultrasonic moving image can be displayed. The frame memory stores an ultrasonic image of one frame. An image currently stored in the frame memory is displayed on the monitor 14. An overwrite in the frame memory is stopped by, e.g., pressing the freeze ON button of the operation input device 13. The video converter executes video format conversion of image data received from the frame memory.

On the basis of mode selection, ROI setting, or transmission start/end input by the user through the input device 13 or another interface, the control processor 27 reads out the transmission/reception conditions and device control program stored in the internal storage device 29 and statically or dynamically controls the ultrasonic diagnostic apparatus in accordance with the conditions and program.

The control processor 27 also reads out a dedicated program stored in the internal storage device 29 and controls the transmission/reception unit 20 and addition processing unit 21 in accordance with the program to implement the fundamental wave component & motion artifact component reducing function and ultrasonic transmission/reception function for residual multiplex reduction (both will be described later).

The image storage unit 28 records image data (still image or moving image) received from the image memory circuit 25 under the control of the control processor 27.

The internal storage device 29 stores the control program of the apparatus, diagnostic protocols, various kinds of data such as transmission/reception conditions, and collected image data. The internal storage device 29 also stores various kinds of subprograms (activities) to implement each processing of a series of examination procedures and a control program to control the apparatus in accordance with the examination procedures (work flow) including the various kinds of activities.

The monitor 14 displays, as an image, morphologic information or blood flow information in a living body on the basis of the video signal from the image memory circuit 25. An image displayed on the monitor 14 is recorded in, e.g., the image storage unit 28 by using corresponding image data stored in the frame memory in the image memory circuit 25.

(Fundamental Wave Component & Motion Artifact Component Reducing Function)

The fundamental wave component & motion artifact component reducing function of the ultrasonic diagnostic apparatus 10 will be described next. In this function, ultrasonic waves are transmitted in at least three rates by inverting the phase by 180° in THI using a difference tone. Obtained echo signals are added in accordance with a predetermined weight, thereby reducing the fundamental wave component and motion artifact component from the difference tone component.

Figure 2:
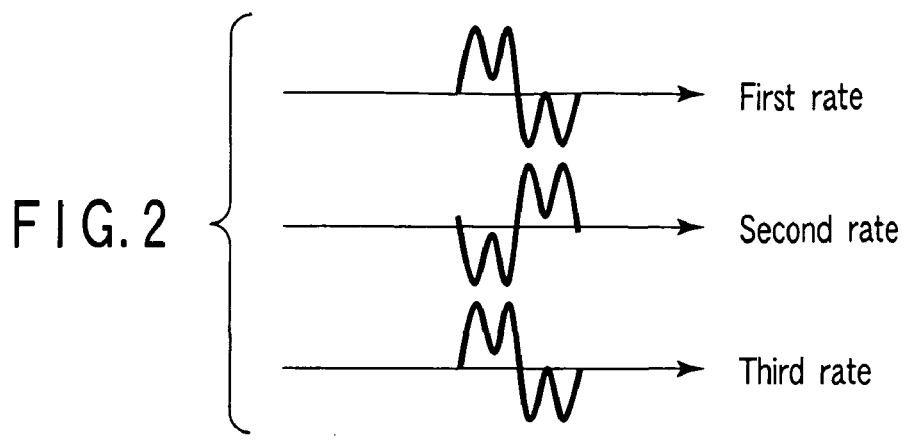
FIG. 2 is a view for explaining ultrasonic transmission by a fundamental wave component & motion artifact component reducing function.

FIG. 2 is a view for explaining ultrasonic transmission by this function. As shown in FIG. 2, ultrasonic waves are transmitted in three rates by changing the phase by 180° such that, for example, the first rate has a negative phase (negative polarity), the second rate has a positive phase (positive polarity), and the third rate has a negative phase. As the transmission waveform of each rate, a combined wave having a plurality of frequencies and phases (a combined wave of a plurality of fundamental waves having different frequencies or phases) is used to generate a difference tone.

In reception of echo signals from the subject, echo signal addition processing is executed by using arbitrary weighting coefficients such as +0.5, +1.0, and +0.5 for the respective rates so that 0 is obtained by addition using the polarity of each echo signal (or transmission ultrasonic wave) as the sign. The weighting can be implemented by gain control at the time of reception.

Figure 3:
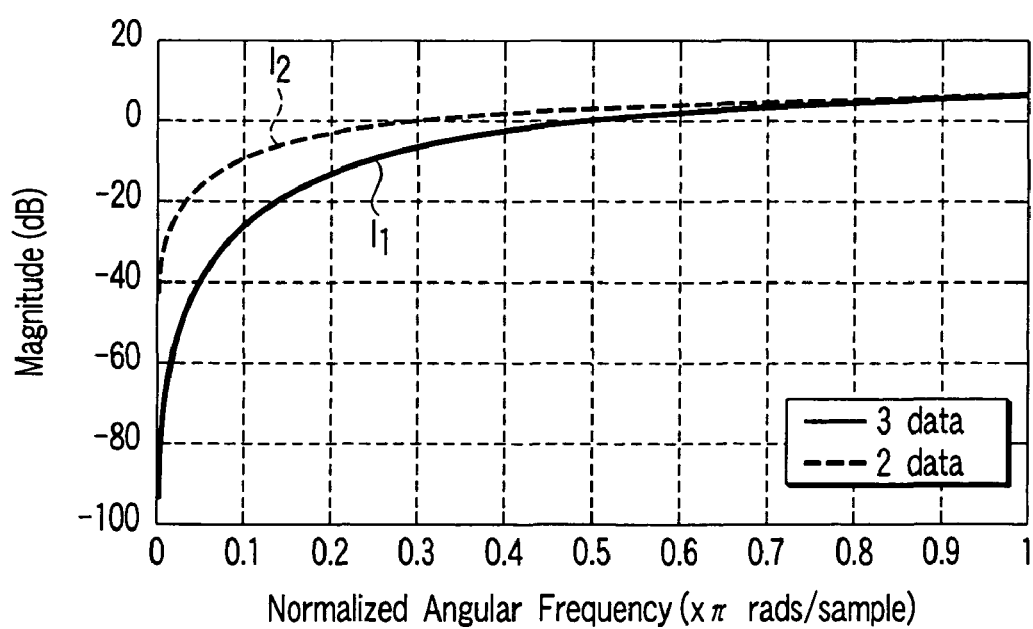
FIG. 3 is a graph showing the characteristic of an echo signal I1 obtained by weighted addition processing.

FIG. 3 is a graph showing the characteristic of an echo signal I1 obtained by weighted addition processing. FIG. 3 also shows the characteristic of a signal I2 obtained by normal pulse inversion (i.e., a signal obtained when ultrasonic waves are transmitted in two rates by changing the phase by 180° such that the first rate has a negative phase, and the second rate has a positive phase, and the signals respectively weighted by +1 and +1 are added).

As shown in FIG. 3, the signal I1 obtained by transmission/reception and weighting of this embodiment exhibits the same behavior as an MTI filter (or high-pass filter) characteristic. As compared to the characteristic of the signal I2 obtained by normal pulse inversion, the signal I1 rises steeply in the low-frequency region. Hence, the band where a motion artifact component is generated (the fundamental wave frequency band and its vicinity) can more properly be separated.

In this function, ultrasonic waves are transmitted in three rates by changing the phase by 180°. In addition processing of obtained echo signals, the weighting coefficients are assigned such that the sum including the polarities becomes 0. Hence, the fundamental wave components contained in echo signals are always canceled between the three rates. Hence, the fundamental wave component superimposed on the difference tone component can be reduced while maintaining the difference tone component.

Ultrasonic transmission to implement the fundamental wave component & motion artifact component reducing function and weighted addition of echo signals obtained by the transmission can be generalized in the following manner.

The number of weighting coefficients equals the number of transmission rates. The coefficients are determined such that their sum becomes 0. In transmission, a rate to which a negative weighting coefficient is assigned is transmitted by controlling its phase to a negative polarity. A rate to which a positive weighting coefficient is assigned is transmitted by controlling its phase to a positive polarity. Since the polarities of transmission waveforms are used in place of the polarities of weighting coefficients, all weighting coefficients in weighted addition are converted to the plus sign (or absolute values). The present invention is not limited to the above-described order and contents of processing if almost the same result as in the generalization is obtained.

(Operation)

Figure 4:
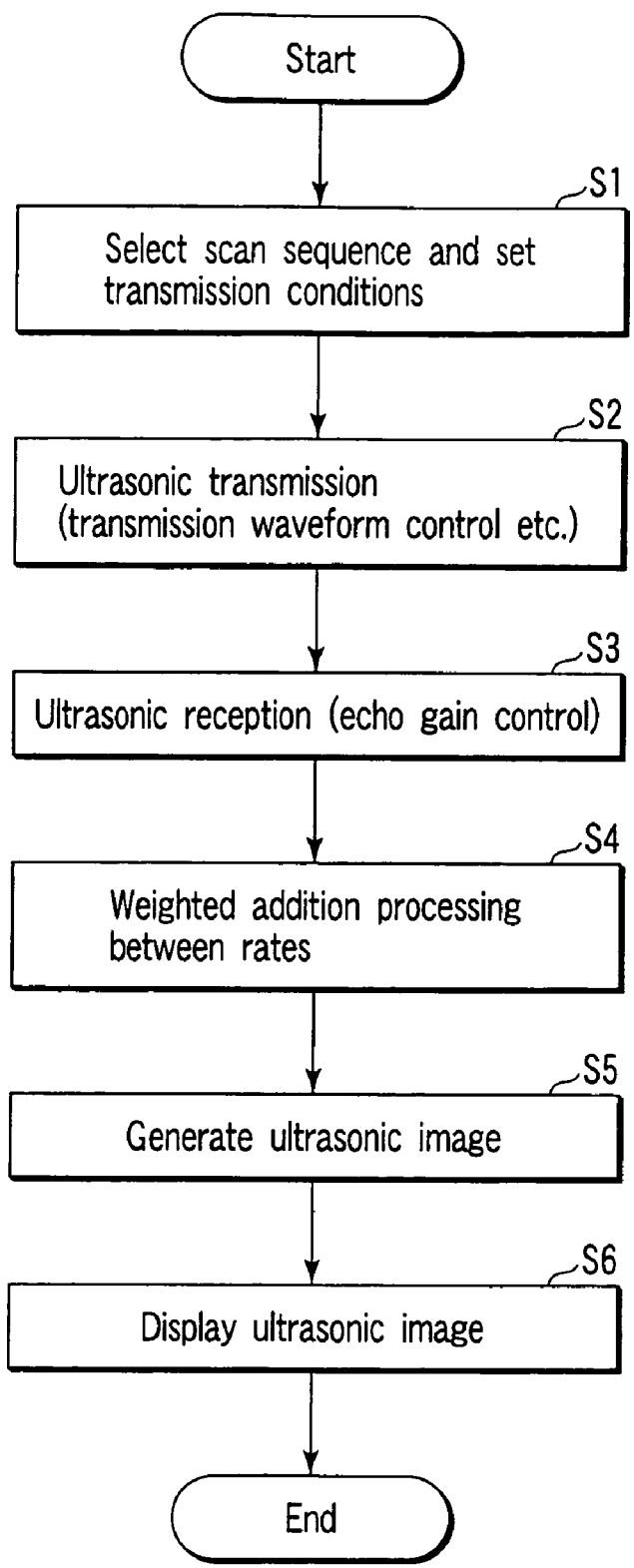
FIG. 4 is a flowchart showing the flow of processing executed in THI using a difference tone.

The imaging operation of the ultrasonic diagnostic apparatus 10 in THI using a difference tone will be described next. FIG. 4 is a flowchart showing the flow of processing executed in THI using a difference tone. As shown in FIG. 4, a scan sequence is selected through the input device 13, and transmission conditions and the like are set (step S1). In this embodiment, in THI using a difference tone, a scan sequence to execute the fundamental wave component & motion artifact component reducing function is selected.

Under the control of the control processor 27, ultrasonic transmission is executed in at least three rates by changing the phase by 180° (step S2). Ultrasonic reception is executed while assigning a weighting coefficient to each rate by gain control at the time reception such that the sum becomes 0 (step S3). Weighted addition processing between the rates is executed (step S4). A thus obtained echo signal exhibits the characteristic shown in FIG. 3, as described above.

An ultrasonic image is generated on the basis of the echo signal obtained by addition processing (step S5). The obtained image is displayed on the monitor 14 (step S6).

Figure 5A:
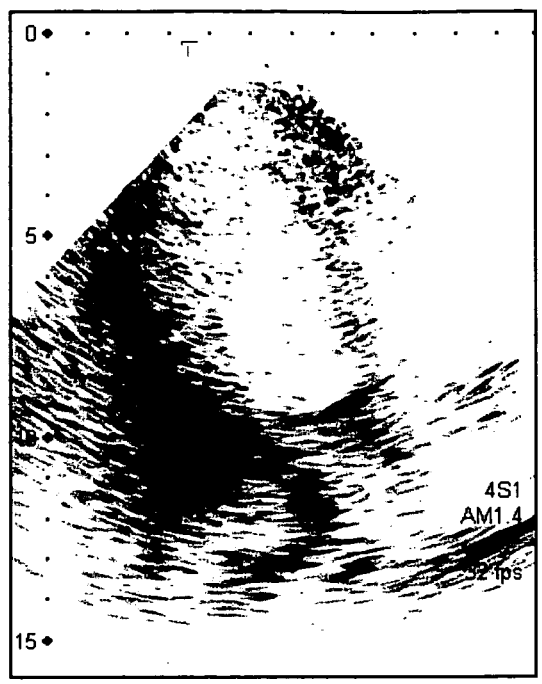
FIGS. 5A and 5B are views showing ultrasonic images (photos) using a signal obtained by normal pulse inversion in THI using a difference tone.
Figure 5B:
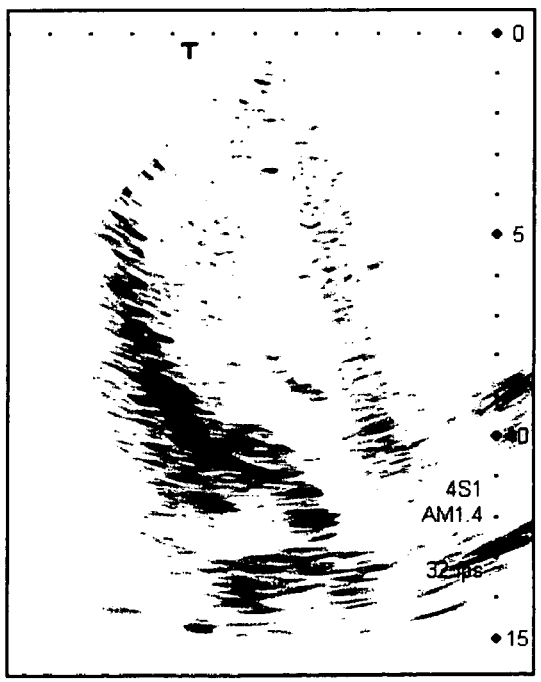

FIGS. 5A and 5B show ultrasonic images (photos) generated by visualizing a circulatory organ (heart) by using a signal (e.g., the signal I2 in FIG. 3) obtained by normal pulse inversion in THI using a difference tone. In the time phase shown in FIG. 5A when the circulatory organ quickly moves, the circulatory organ flickers because of the influence of the motion artifact component generated in the fundamental wave component, as compared to the time phase shown in FIG. 5B when the circulatory organ slowly moves.

Figure 6A:
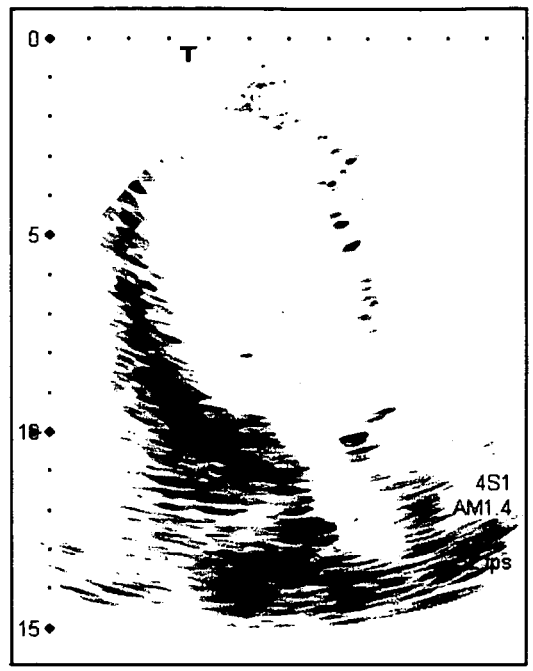
FIGS. 6A and 6B are views showing the photos of ultrasonic images obtained by an imaging operation according to the first embodiment.
Figure 6B:
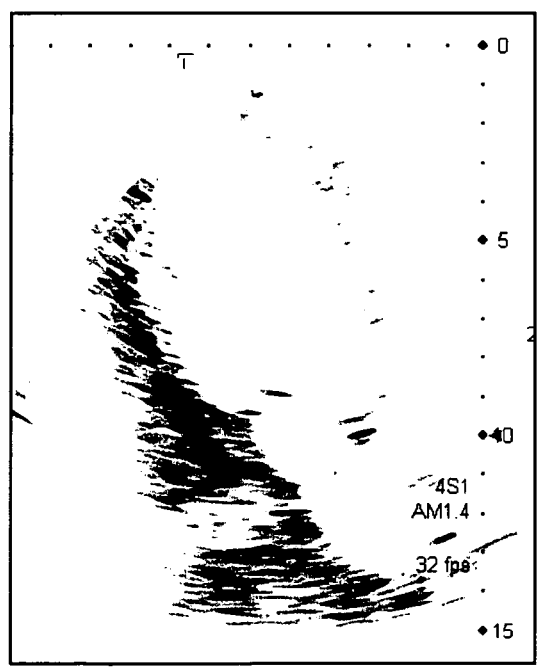

FIGS. 6A and 6B are views showing the photos of ultrasonic images (the transmission conditions and the like are the same as in FIGS. 5A and 5B) obtained by the imaging operation of this embodiment. FIG. 6A corresponds to the time phase when the circulatory organ quickly moves, and FIG. 6B corresponds to the time phase when the circulatory organ slowly moves. As shown in FIGS. 6A and 6B, in the ultrasonic images obtained by the imaging operation of this embodiment, the flicker caused by the motion artifact component is eliminated, as compared to the images in FIGS. 5A and 5B.

According to the above-described arrangement, the following effects can be obtained.

According to this ultrasonic diagnostic apparatus, in THI using a difference tone, ultrasonic waves are transmitted in at least three rates by inverting the phase, and obtained echo signals are added by using predetermined weights. Hence, an MTI filter function which cancels the fundamental wave component and exhibits a proper characteristic is achieved. As a result, the fundamental wave component and motion artifact component can be reduced from the difference tone component. Even when tissue with quick motion is visualized, an excellent ultrasonic image can be provided.

The method implemented by the ultrasonic diagnostic apparatus requires no new hardware configuration such as a filter circuit. The method can be practiced by newly installing, in the existing system, software to implement the fundamental wave component & motion artifact component reducing function. Hence, in THI using a difference tone, excellent visualization of tissue with quick motion can be implemented easily at a relatively low cost.

Second Embodiment

The second embodiment of the present invention will be described next. An ultrasonic diagnostic apparatus according to this embodiment provides a proper diagnostic image by reducing residual multiplex generated in transmission in a plurality of rates. Residual multiplex is a phenomenon that an echo signal from a region outside the range gate is superimposed as a residual ultrasonic wave on a rate after the rates of ultrasonic transmission. For the descriptive convenience, a signal generated in a rate of a succeeding stage by residual multiplex will be referred to as a residual multiplex component hereinafter.

FIG. 7 is a view for explaining ultrasonic transmission/reception which is executed for residual multiplex reduction by the ultrasonic diagnostic apparatus. As shown in FIG. 7, in the ultrasonic transmission, in addition to the same ultrasonic reception as in the first embodiment (i.e., ultrasonic transmission in three rates by changing the phase by 180° and reception with gains of +0.5, +1.0, and +0.5), a rate for not transmission but only reception is inserted at the end. The gain of the rate for only reception is controlled such that the residual ultrasonic component becomes 0 when addition is executed by using weights including the polarities of the respective rates (i.e., in the example shown in FIG. 7, the gain of the fourth rate is −0.5). When thus obtained echo signals of the respective rates are finally added, the residual multiplex components can be canceled between the rates. Hence, residual multiplex can be reduced.

Ultrasonic transmission/reception for residual multiplex reduction can be generalized in the following manner. In addition to ultrasonic transmission/reception generalized in the first embodiment, a rate for not transmission but only reception is inserted at the end. The number of rates to be inserted can be determined by the depth of a residual ultrasonic wave (echo signal) to be canceled. The gain of the rate for only reception is controlled such that the residual multiplex component becomes 0 when addition is executed by using weights of the respective rates.

According to the above-described arrangement, residual multiplex generated in transmission in a plurality of rates can be reduced, and an excellent diagnostic image can be provided. When this method is combined with the method described in the first embodiment, in THI using a difference tone, an excellent ultrasonic image can be provided by reducing the fundamental wave component, motion artifact component, and residual multiplex.

Third Embodiment

The third embodiment of the present invention will be described next. According to an ultrasonic diagnostic apparatus of this embodiment, in the fundamental wave component reducing function described in the first or second embodiment, weighting coefficients in echo signal addition are adaptively controlled on the basis of a predetermined standard. The adaptive control of weighting coefficients may be executed on the basis of any standard. In the following embodiment, for the sake of a concrete explanation, in heart diagnosis using the fundamental wave component reducing function according to the first embodiment, the cardiac time phase at the time of ultrasonic scanning is determined on the basis of an ECG waveform, and weighting coefficients in echo signal addition are adaptively controlled in accordance with the cardiac time phase.

Figure 8:
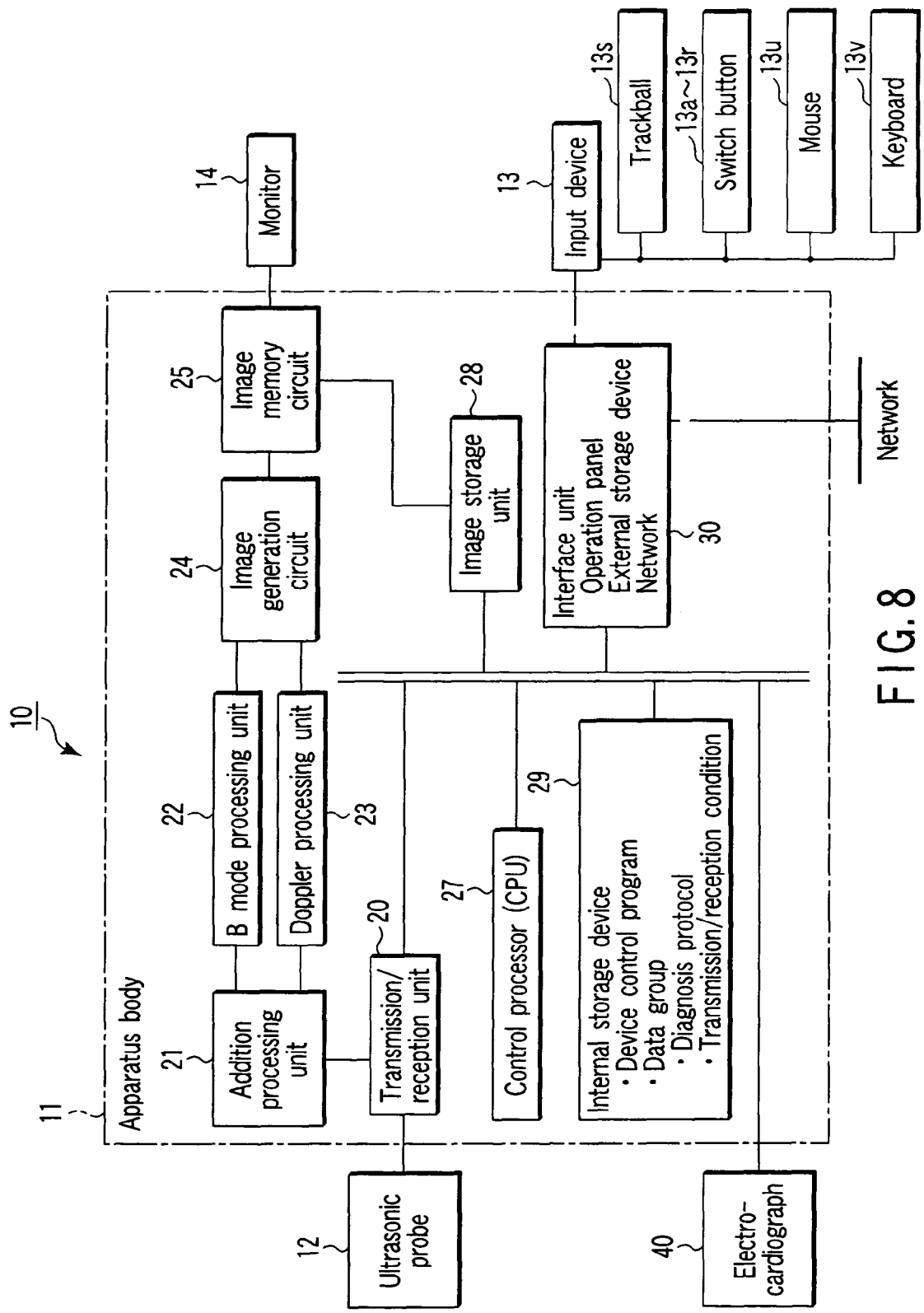
FIG. 8 is a block diagram showing an ultrasonic diagnostic apparatus 10 according to the third embodiment.

FIG. 8 is a block diagram of an ultrasonic diagnostic apparatus 10 according to this embodiment. As shown in FIG. 8, the ultrasonic diagnostic apparatus 10 further comprises an electrocardiograph 40.

The electrocardiograph (ECG) 40 measures a graph which records a time change in electrical phenomenon of the heart of a subject, i.e., an electrocardiogram (ECG waveform). The ECG waveform signal detected by the electrocardiograph 40 is automatically stored in an image storage unit 28, and if necessary, sent to a monitor 14 through an image memory circuit 25 and displayed as an ECG waveform.

An internal storage device 29 stores a weighting coefficient table which makes cardiac time phases correspond to weighting coefficients in echo signal addition processing, as shown in FIG. 9.

A control processor 27 determines the cardiac time phase on the basis of the ECG waveform acquired from the electrocardiograph 40. The control processor 27 also determines, for each frame, weighting coefficients corresponding to the cardiac time phase on the basis of the determination result and the weighting coefficient table. The control processor 27 also controls an addition processing unit 21 to execute addition processing by using the determined weighting coefficient.

(Adaptive Control of Weighting Coefficients)

FIG. 10 is a view showing an ECG waveform so as to explain the concept of adaptive control of the weighting coefficients. In the example shown in FIG. 10, the heart beat movement is classified into four states, i.e., a state wherein the heart almost stands (periods T2 and T6), a uniform motion state (periods T4 and T8), a positive accelerated motion state (periods T3 and T7), and a negative accelerated motion state (periods T1 and T5).

In the adaptive control of weighting coefficients, the cardiac time phase is determined on the basis of the ECG waveform detected at the time of ultrasonic scanning. Weighting coefficients in echo signal addition are determined on the basis of the determination result and the weighting coefficient table. For example, when an ECG waveform detected at the time of ultrasonic scanning related to a given frame belongs to the period T3 or T7, weights in addition processing related to that frame are 0.7 for the first rate, 1 for the second rate, and 0.3 for the third rate. The reason why the weighting coefficients are assigned in this way is to reduce the influence of a motion artifact and residual wave component generated by the difference in heart beat movement velocity between the rates. When the weighting coefficient is 0, ultrasonic transmission or ultrasonic reception is not executed in this rate.

(Operation)

Figure 11:
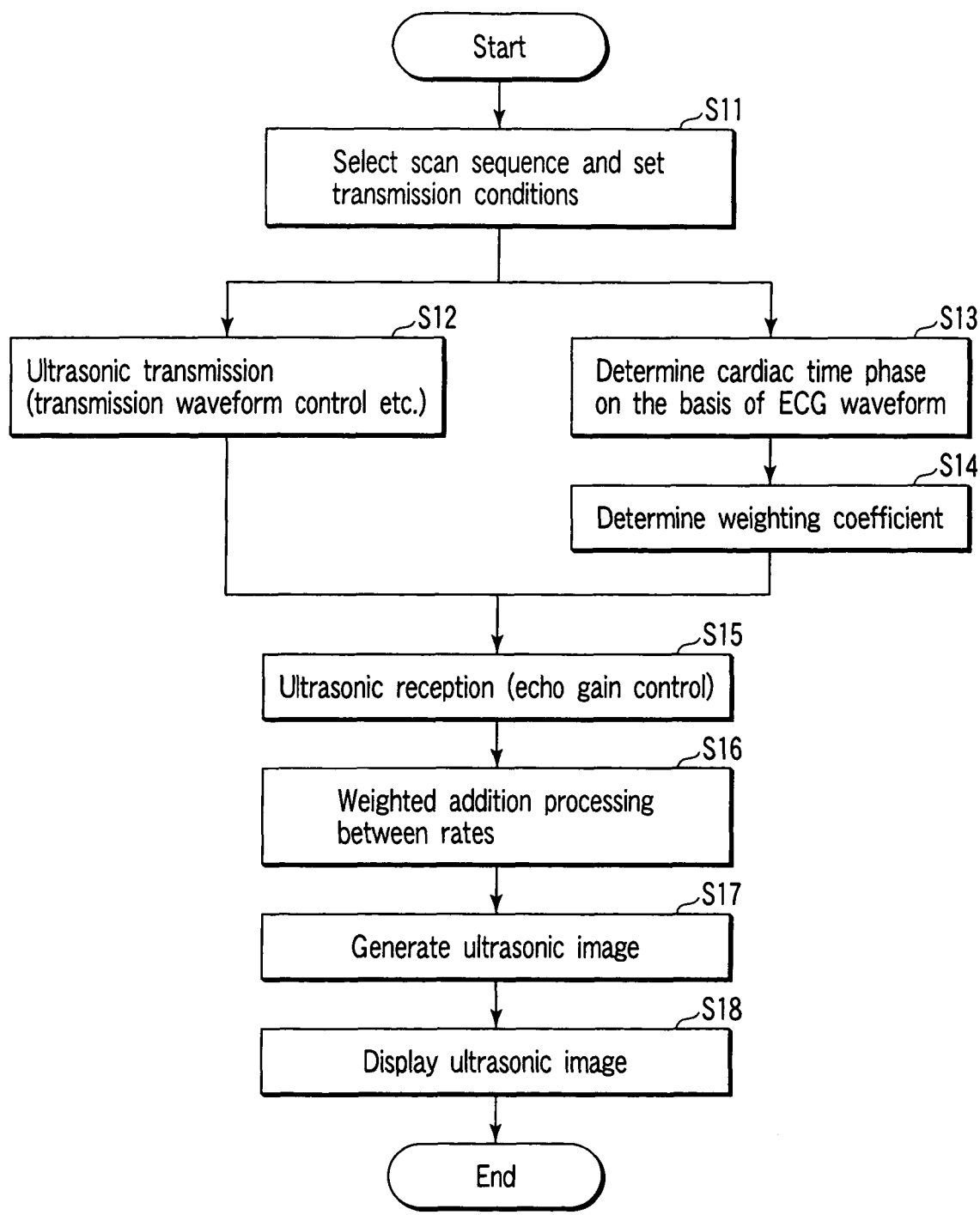
FIG. 11 is a flowchart showing the flow of processing executed in THI using a difference tone.

An imaging operation in THI using the adaptive control of weighting coefficients will be described next. FIG. 11 is a flowchart showing the flow of processing executed in THI using a difference tone. As shown in FIG. 11, a scan sequence is selected, and transmission conditions and the like are set. After that, ultrasonic transmission is executed in at least three rates by changing the phase by 180° (steps S11 and S12). The operations in these steps are the same as in steps S1 and S2 shown in FIG. 4.

The control processor 27 determines the cardiac time phase of each frame on the basis of the ECG waveform acquired from the electrocardiograph 40 (step S13) and determines weighting coefficients in addition processing on the basis of the determination result and the weighting coefficient table (step S14).

Ultrasonic reception is executed while assigning the weighting coefficients determined by the control processor 27 (step S15). Weighted addition processing between the rates is executed (step S16). An ultrasonic image is generated on the basis of the echo signal obtained by addition processing (step S17). The obtained image is displayed on the monitor 14 (step S18).

According to the above-described arrangement, weighting coefficients in echo signal addition are adaptively controlled on the basis of a predetermined standard such as an ECG waveform. Hence, the influence of a motion artifact and the like generated by the difference in heart beat movement velocity between rates can be reduced, and an excellent ultrasonic image can be provided.

Note that the present invention is not exactly limited to the above embodiments, and constituent elements can be modified in the execution stage without departing from the spirit and scope of the invention. Detailed modifications are as follows.

(1) Each function according to the embodiments can be implemented even by installing a program to execute the processing in a computer such as a workstation and expanding the program on the memory. The program capable of causing the computer to execute the method may be stored in a recording medium such as a magnetic disk (e.g., a floppy disk or hard disk), optical disk (e.g., a CD-ROM or DVD), or semiconductor memory and distributed.

(2) Each of the above embodiments has exemplified the case of using the transmission ultrasonic wave which is formed by combining at least a first fundamental wave and a second fundamental wave as a higher harmonic wave than the first fundamental wave in at least three rates by alternately inverting a phase by 180°. However, the present invention is not limited to this. For example, it is possible to acquire the same effect according to the configuration that the transmission ultrasonic wave, which is formed by combining at least a first fundamental wave and a second fundamental wave as a higher harmonic wave than the first fundamental wave, is transmitted to each of a plurality of scan lines in at least three rates and in such a way to include at least a phase inverting by 180° in each embodiment.

Various inventions can be formed by properly combining a plurality of constituent elements disclosed in the above embodiments. For example, several constituent elements may be omitted from all the constituent elements described in the embodiments. In addition, constituent elements throughout different embodiments may be properly combined.

What is claimed is:

1. An ultrasonic diagnostic apparatus, comprising:
a transmission unit which transmits, to each of a plurality of scan lines, a plural number of ultrasonic waves not less than three, each ultrasonic wave being formed from a combined ultrasonic wave, the ultrasonic waves including at least a wave having a phase inversion by 180°, the combined ultrasonic wave being formed by combining at least a first fundamental wave and a second fundamental wave as a higher harmonic wave than the first fundamental wave;
a reception unit which receives echo signals which correspond to the plural number of transmitted ultrasonic waves from each of the plurality of scan lines;
an addition processing unit which adds the received echo signals for each of the plurality of scan lines by using predetermined weighting coefficients; and
a generation unit which generates ultrasonic image data by using a difference tone component contained in the added echo signal.

2. The apparatus according to claim 1, wherein the addition processing unit assigns the weighting coefficients to the received echo signals for each of the plurality of scan lines so as to nullify a sum between the received echo signals for each of the plurality of scan lines.

3. The apparatus according to claim 2, further comprising:
a weighting coefficient determination unit which determines a cardiac time phase based on an ECG waveform of a subject using an electrocardiograph and determines the weighting coefficients of each cardiac time phase using a table that makes cardiac time phases correspond to the weighting coefficients, wherein
the addition processing unit adds the received echo signals for each of the plurality of scan lines by using the determined weighting coefficients.

4. The apparatus according to claim 1, wherein
the transmission unit transmits, to each of the plurality of scan lines, the plural number of ultrasonic waves and then starts transmitting the ultrasonic waves to a subsequent scan line after a period of time corresponding to a pulse repetition frequency has elapsed, and
the addition processing unit adds the received echo signals for each of the plurality of scan lines by using the predetermined weighting coefficients.

5. The apparatus according to claim 4, wherein the addition processing unit assigns a weighting coefficient to at least one of the received echo signals in a period in which an ultrasonic wave is not transmitted so as to nullify a sum of residual multiplex components superimposed on the transmitted ultrasonic waves for each of the plurality of scan lines.

6. The apparatus according to claim 5, further comprising:
a weighting coefficient determination unit which determines a cardiac time phase based of an ECG waveform of a subject using an electrocardiograph and determines the weighting coefficients of each cardiac time phase using a table which makes cardiac time phases correspond to the weighting coefficients, wherein
the addition processing unit adds the received echo signals for each of the plurality of scan lines by using the determined weighting coefficients.

7. The ultrasonic diagnostic apparatus of claim 1, wherein the transmission unit transmits an odd number of ultrasonic waves not less than three, to each of the plurality of scan lines.

8. An ultrasonic diagnostic apparatus control method comprising:
transmitting, to each of a plurality of scan lines, a plural number of ultrasonic waves not less than three, each ultrasonic wave being formed from a combined ultrasonic wave, the ultrasonic waves including a wave having at least a phase inverting by 180°, the combined ultrasonic wave being formed by combining at least a first fundamental wave and a second fundamental wave as a higher harmonic wave than the first fundamental wave;
receiving echo signals which correspond to the plural number of transmitted ultrasonic waves from each of the plurality of scan lines;
adding the received echo signals of the plurality of scan lines for each by using predetermined weighting coefficients; and
generating ultrasonic image data by using a difference tone component contained in the added echo signal.

9. The method according to claim 8, wherein in the adding, the weighting coefficients are assigned to the received echo signals so as to nullify a sum between the received echo signals for each of the plurality of scan lines.

10. The method according to claim 9, further comprising:
obtaining an ECG waveform of a subject; and
determining a cardiac time phase on the basis of an ECG waveform of a subject and determining the weighting coefficients for the respective rates on the basis of a determination result, wherein
in the adding step, the received echo signals are added for each of the plurality of scan lines by using the determined weighting coefficients.

11. The method according to claim 8, wherein,
in the transmitting step, the plural number of ultrasonic waves are transmitted to each of the plurality of scan lines, and then the ultrasonic waves are transmitted to a subsequent scan line after a period of time corresponding to a pulse repetition frequency has elapsed, and
in the adding step, the received echo signals are added for each of the plurality of scan lines by using the predetermined weighting coefficients.

12. The method according to claim 11, wherein in the adding step, a weighting coefficient is assigned to at least one of the received echo signals so as to nullify a sum of residual multiplex components superimposed on the transmitted ultrasonic waves for each of the plurality of scan lines.

13. The method according to claim 12, further comprising:
obtaining an ECG waveform of a subject; and
determining a cardiac time phase based on an ECG waveform of a subject and determining the weighting coefficients for the respective rates based on a determination result, wherein
in the adding step, the received echo signals are added for each of the plurality of scan lines by using the determined weighting coefficients.

* * * * *